United States Patent [19]

Rivier et al.

[11] Patent Number: 5,262,519
[45] Date of Patent: Nov. 16, 1993

[54] GRF ANALOGS XI

[75] Inventors: Jean E. F. Rivier; Wylie W. Vale, Jr., both of La Jolla, Calif.

[73] Assignee: The Salk Institute for Biological Studies, San Diego, Calif.

[21] Appl. No.: 701,414

[22] Filed: May 15, 1991

[51] Int. Cl.$^5$ ............... A61K 37/02; A61K 37/00; C07K 5/00; C07K 7/00
[52] U.S. Cl. .................................................. 530/324
[58] Field of Search ..................... 514/12; 530/324

[56] References Cited

U.S. PATENT DOCUMENTS

| | | | |
|---|---|---|---|
| 4,649,131 | 3/1987 | Felix et al. | 514/12 |
| 4,689,318 | 8/1987 | Kaiser et al. | 514/12 |
| 4,843,064 | 6/1989 | Vaughan et al. | 514/12 |
| 5,002,931 | 3/1991 | Rinier et al. | 514/12 |
| 5,043,322 | 8/1991 | Rinier et al. | 514/12 |

FOREIGN PATENT DOCUMENTS 9012810 11/1990 PCT Int'l Appl. .

*Primary Examiner*—Lester L. Lee
*Assistant Examiner*—A. M. Davenport
*Attorney, Agent, or Firm*—Fitch, Even, Tabin & Flannery

[57] ABSTRACT

The invention provides synthetic peptides which are extremely potent in stimulating the release of pituitary GH in animals, including humans and also resist enzymatic degradation in the body. Certain preferred peptides have the formula:

(B)$R_1$-Ala-Asp-Ala-Ile-Phe-Thr-$R_8$-Ser-Tyr-Arg-Lys-Val-Leu-$R_{15}$-$R_{16}$- Leu-Ser-Ala-Arg-Lys-Leu-Leu-$R_{24}$-$R_{25}$-Ile-Nle-$R_{28}$-Arg-Y wherein $R_1$ is Tyr, D-Tyr, Phe, D-Phe, His or D-His; B is H or N$^\alpha$Me; $R_8$ is Ala, Aib or Asn; $R_{15}$ is Gly or Ala; $R_{16}$ is Ala, Aib or Gln; $R_{24}$ is Ala, Aib or Gln; $R_{25}$ is Ala, Aib or Asp; $R_{28}$ is Ser or Asn; Y is NHR with R being H or lower alkyl; provided that at least one of $R_8$, $R_{16}$, $R_{24}$ and $R_{25}$ is Ala or Aib.

20 Claims, No Drawings

GRF ANALOGS XI

This invention was made with Government support under grant number DK-26741 awarded by the National Institutes of Health. The Government has certain rights in this invention.

The present invention relates to peptides having influence on the function of the pituitary gland in humans and other animals. In particular, the present invention is directed to peptides which promote the release of growth hormone by the pituitary gland.

BACKGROUND OF THE INVENTION

Physiologists have long recognized that the hypothalamus controls the secretory functions of the adenohypophysis with the hypothalamus producing special substances which stimulate or inhibit the secretion of each pituitary hormone. A hypothalamic inhibitory factor was characterized in 1972 in the form of somatostatin which inhibits the secretion of growth hormone(GH). In 1982, growth hormone releasing factors (GRF) were isolated from extracts of human pancreatic tumors, purified, characterized, synthesized and tested; they were found to promote the release of GH by the pituitary. Human hypothalamic GH releasing factor was subsequently found to have precisely the same structure which is now referred to by the term hGRF(1-44)-NH$_2$ which has the following formula: (SEQ ID NO:1) Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Gl u-Ser-Asn-Gln-Glu-Arg-Gly-Ala-Arg-Ala-Arg-Leu, wherein the C-terminus is amidated. Rat GRF(1-43)-OH was later found to have the following formula: (SEQ ID NO:2) His-Ala-Asp-Ala-Ile-Phe-Thr-Ser-Ser-Tyr-Arg-Arg-Ile-Leu-Gly-Gln-L eu-Tyr-Ala-Arg-Lys-Leu-Leu-His-Glu-Ile-Met-Asn-Arg-Gln-Gln-Gly-Glu-Arg-Asn-Gln-Glu-Gln-Arg-Ser-Arg-Phe-Asn. Many analogs of these native structures have been synthesized.

SUMMARY OF THE INVENTION

Synthetic polypeptides have now been synthesized and tested which release GH from cultured pituitary cells, which have increased resistance to enzymatic degradation in the body, and which exhibit very substantially increased potency. These advantageous properties result from the peptides having an alpha-helical form of increased stability, which peptides have L-alanine in one or more of positions 8, 16, 24 and 25 that is unsubstituted or substituted with a methyl group on its alpha carbon atom (C$^\alpha$Me or C$^{60}$ CH$_3$), and Preferably at least the 8-position is so substituted. Ala having its alpha carbon atom substituted with a methyl group is indicated by the abbreviation Aib (for 2-aminoisobutyric acid).

In addition to the foregoing, the peptides may contain other substitutions for various residues found in the native hormones. For example, D-Ala, N$^\alpha$CH$_3$-D-Ala (D-NMA) or NMA may be substituted in the 2-position, and these are considered to be equivalents of L-Ala. Either C$^\alpha$MeLeu(CML) or Nle is preferably present instead of Met in the 27-position; however, D-Met or Nva or other residues may be present and are considered equivalents. The peptides may also have any one of the following residues in the ;-position: Tyr, D-Tyr, Phe, D-Phe, His and D-His, which residue may optionally have a methyl substitution either on the alpha-carbon or in the alpha-amino group, or the alpha-amino group may be deleted(desamino); this residue may also have its alpha-amino group acylated, preferably by acetyl(Ac) or formyl(For), all of which are considered to be equivalents to the unsubstituted residues. The peptides may optionally contain other substitutions as are known in the art, e.g., D-Asp at the 3-position and/or Arg at the 12-position and/or Phe or D-Tyr at the 10-position and/or Ala at the 15-position and/or Asn or Ala in the 28-position, all of which are considered equivalents.

Pharmaceutical compositions in accordance with the invention include such analogs which are between about 29 and 44 residues in length, or a nontoxic salt of any of these, dispersed in a pharmaceutically or veterinarily acceptable liquid or solid carrier. Such pharmaceutical compositions can be used in clinical medicine, both human and veterinary, for administration for therapeutic purposes, and also diagnostically. Moreover, they can be used to promote the growth of warm blooded animals, including fowl, and in aquiculture.

DETAILED DESCRIPTION OF PREFERRED EMBODIMENTS

The nomenclature used to define the peptides is that specified by Schroder & Lubke, "The Peptides", Academic Press (1965), wherein in accordance with conventional representation the amino group at the N-terminus appears to the left and the carboxyl group at the C-terminus to the right. By natural amino acid is meant one of common, naturally occurring amino acids found in proteins comprising Gly, Ala, Val, Leu, Ile, Ser, Thr, Lys, Arg, Asp, Asn, Glu, Gln, Cys, Met, Phe, Tyr, Pro, Trp and His. By Nle is meant norleucine, and by Nva is meant norvaline. Where the amino acid residue has isomeric forms, it is the L-form of the amino acid that is represented unless otherwise expressly indicated. D-NMA signifies the D-isomer of alanine wherein the alpha-amino group is substituted by methyl.

The invention generally provides synthetic peptides having the following sequence (I): SEQ ID NO:14, Xaa-Xaa-Xaa-Ala-Xaa-Phe-Thr-Xaa-Xaa-Xaa-Arg-Xaa-Xaa-Leu-Xaa-Xaa-Leu-Xaa-Ala-Arg-Xaa-Xaa-Leu-Xaa-Xaa-Xaa-Xaa-Xaa-Ar g-Gln-Gln-Gly-Glu-Xaa-Asn-Gln-Glu-Xaa-Xaa-Xaa-Arg-Xaa-Xaa-Xaa, with the Xaa groups being more particularly defined with reference to the following formula: (B)R$_1$-R$_2$-R$_3$-Ala-R$_5$-Phe-Thr-R$_8$-R$_9$-R$_{10}$-Arg-R$_{12}$-R$_{13}$-Leu-R$_{15}$-R$_{16}$-L eu-R$_{18}$-Ala-Arg-r$_{21}$-R$_{22}$-Leu-R$_{24}$-R$_{25}$-R$_{26}$-R$_{27}$-R$_{28}$-Arg-Gln-Gln-Gly-Glu-R$_{34}$-Asn-Gln-Glu-R$_{38}$-R$_{39}$-R$_{40}$-Arg-R$_{42}$-R$_{43}$-R$_{44}$ wherein R$_1$ is Tyr, D-Tyr, Met, Phe, D-Phe, pCl-Phe, Leu, His or D-His; B is H, C$^\alpha$e, N$^\alpha$Me, desamino, Ac or For; R$_2$ is Ala, D-Ala, NMA or D-NMA; R$_3$ is Asp or D-Asp; R$_5$ is Ile or Leu; R$_8$ is Ala, Aib, Ser or Asn; R$_9$ is Ser, Ala or Aib; R$_{10}$ is Tyr, D-Tyr or Phe; R$_{12}$ is Arg or Lys; R$_{13}$ is Ile, Val, Leu or Ala; R$_{15}$ is Gly or Ala; R$_{16}$ is Ala, Aib or Gln; R$_{18}$ is Ser or Tyr; R$_{21}$ is Lys, D-Lys, Arg or D-Arg; R$_{22}$ is Leu, Ile, Ala, Aib or Val; R$_{24}$ is Ala, Aib, Gln or His; R$_{25}$ is Ala, Aib, Asp or Glu; R$_{26}$ is Ile or Leu; R$_{27}$ is Met, D-Met, Ala, Nle, Ile, Leu, Nva or Val; R$_{28}$ is Asn, Ala, Aib or Ser; R$_{34}$ is Ser or Arg; R$_{38}$ is Arg or Gln; R$_{39}$ is Gly or Arg; R$_{40}$ is Ala or Ser; R$_{42}$ is Phe, Ala or Val; R$_{43}$ is Asn or Arg; R$_{44}$ is Leu or another L-isomer natural amino acid; provided however that Ala or Aib is present in at least one of R$_8$, R$_{16}$, R$_{24}$ and R$_{25}$. Acceptable C-terminally shortened versions of the peptides can be provided by deleting a sequence of up to 5 residues beginning at the C-terminus, and these may have 2, 3 or all 4 of the specified Ala or Aib substitutions. In one preferred subclass of the foregoing, $R_5$ is Ile, $R_{18}$ is Ser, $R_{24}$ is Gln, $R_{25}$ is Asp, $R_{26}$ is Ile, $R_{34}$ is Ser, $R_{38}$ is Arg, $R_{39}$ is Gly and $R_{40}$ is Ala. If the peptide extends to position-44, $R_{44}$ is preferably Leu or Val.

A preferred subclass of such peptides is the group having the following sequence: SEQ ID NO:15, Xaa-Xaa-Xaa-Xaa-Ala-Ile-Phe-Thr-Xaa-Ser-Tyr-Arg-Xaa-X aa-Leu-Xaa-Xaa-Leu-Ser-Ala-Arg-Xaa-Leu-Leu-Xaa-Xaa-Ile-Xaa-Xaa-Arg, with the Xaa groups being more particularly defined with reference to the following formula: (B)$R_1$-$R_2$-$R_3$-Ala-Ile-Phe-Thr-$R_8$-Ser-Tyr-Arg-$R_{12}$-$R_{13}$-Leu-$R_{15}$-$R_{16}$-Leu-Ser-Ala-Arg-$R_{21}$-Leu-Leu-$R_{24}$-$R_{25}$-Ile-$R_{27}$-$R_{28}$-Arg wherein $R_1$ is Tyr, D-Tyr, Phe, D-Phe, His or D-His; B is H, $C^\alpha$Me or $N^\alpha$Me; $R_2$ is Ala, D-Ala, NMA or D-NMA; $R_3$ is Asp or D-Asp; $R_8$ is ala, Aib, Ser or Asn; $R_{12}$ is Arg or Lys; $R_{13}$ is Ile or Val; $R_{15}$ is gly or Ala; $R_{16}$ is Ala, Aib or Gln; $R_{21}$ is Lys or Arg; $r_{24}$ is Ala, Aib, Gln or His; $R_{25}$ is Ala, Aib, Asp or Glu; $R_{27}$ is Met, D-Met, Ala, Nle, Ile, Leu, Nva or Val; $R_{28}$ is Asn or Ser; provided that at least one of $R_8$, $R_{16}$, $R_{24}$ or $R_{25}$ is Ala or Aib.

In any of these peptides, the carboxyl moiety of the amino acid residue at the C-terminus may be any of the following radicals (all of which are considered to be equivalents): —COOR,—CRO,—CONHNHR,—CON(R)(R') or —CH$_2$OR, with R and R' being lower alkyl, fluoro lower alkyl or hydrogen; methyl, ethyl and propyl are the preferred lower alkyl groups. Preferably it is -CONHR, with R being H or lower alkyl.

Still another preferred subclass of peptides provided by the invention are those according to the formula: SEQ ID NO:16, Xaa-Ala-Asp-Ala-Ile-Phe-Thr-Xaa-Ser-Tyr-Arg-Lys-Val-Leu-X aa-Xaa-Leu-Ser-Ala-Arg-Xaa-Leu-Leu-Xaa-Xaa-Ile-Xaa-Xaa-Arg-Gln-Gln-Gly with the Xaa groups being more particularly defined with reference to the following formula: (B)$R_1$-Ala-Asp-Ala-Ile-Phe-Thr-$R_8$-Ser-Tyr-Arg-Lys-Val-Leu-$R_{15}$-$R_{16}$-Leu-Ser-Ala-Arg-$R_{21}$-Leu-Leu-$R_{24}$-$R_{25}$-Ile-Nle-$R_{28}$-Arg-Gln-Gln-Gly-Y wherein $R_1$ is Tyr, D-Tyr, Phe, D-Phe, His or D-His; B is H or $N^\alpha$Me; $R_8$ is Ala, Aib or Asn; $R_{15}$ is Gly or Ala; $R_{16}$ is Ala, Aib or Gln; $R_{21}$ is Lys or Arg; $R_{24}$ is Ala, Aib or Gln; $R_{25}$ is Ala, Aib or Asp; $R_{28}$ is Asn or Ser; Y is NHR with R being H or lower alkyl; provided however that Gly, Gln-Gly or Gln-Gln-Gly may be deleted at the C-terminus, and provided also that at least one of $R_8$, $R_{16}$, $R_{24}$ and $R_{25}$ is Ala or Aib, and two or more of such substitutions may be present in these 4 positions. In one particularly preferred group of peptides from this subclass, $R_{21}$ is Lys, and $R_{28}$ is Asn.

As defined above, fragments which extend from the N-terminus through residue-29 have biological potency in effecting the release of GH by the pituitary. Such biologically active fragments of 29 or 32 residues in length which have a C-terminus that is an amide or a substituted amide are most preferred.

The peptides are synthesized by a suitable method, such as by exclusively solid-phase techniques, by partial solid-phase techniques, by fragment condensation or by solution couplings. For example, techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. Solution synthesis is described in detail in the treatise "Methoden der Organischen Chemie (Houben-Weyl): Synthese von Peptiden", E. Wunsch (editor) (1974) Georg Thieme Verlag, Stuttgart, W. Ger. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

In this respect, intermediates can be created having the Formula (II): $X^1$-(B)$R_1$(X or $X^2$)-$R_2$-$R_3$($X^3$)-Ala-$R_5$-Phe-Thr($X^4$)-$R_8$($X^4$ or $X^5$)-$R_9$($X^4$)-$R_{10}$($X^2$)-Arg($X^6$)-$R_{12}$($X^6$ or $X^7$)-$R_{13}$-Leu-$R_{15}$-$R_{16}$($X^5$)-Leu-$R_{18}$($X^2$ or $X^4$)-Ala-Arg($X^6$)-$R_{21}$($X_6$ or $X^7$)-$R_{22}$-Leu-$R_{24}$($X^5$or X)-$R_{25}$($X^3$)-$R_{26}$-$R_{27}$-$R_{28}$($X^4$ or $X^5$)-Arg($X^6$)-Gln($X^5$)-Gln($X^5$)-Gly-Glu($X^3$)-$R_{34}$($X^4$ or $X^6$)-Asn($X^5$)-Gln($X^5$)-Glu($X^3$)-$R_{38}$($X^6$ or $X^5$)-$R_{39}$($X^6$)-$R_{40}$($X^2$)-Arg($X^6$)-$R_{42}$-$R_{43}$($X^5$ or $X^6$)-$R_{44}$($X^8$)-$X^9$ wherein: $X^1$ is either hydrogen or an alpha-amino protecting group. The alpha-amino protecting groups contemplated by $X^1$ are those well known to be useful in the art of stepwise synthesis of polypeptides. Among the classes of alpha-amino protecting groups which may be employed as $X^1$ are (1) aromatic urethan-type protecting groups, such as fluorenylmethyloxycarbonyl (FMOC), benzyloxy-carbonyl(Z) and substituted Z, such as p-chlorobenzy-loxycarbonyl, p-nitrobenzyloxycarbonyl, p-bromobenzy-loxycarbonyl, and p-methoxybenzyl oxycarbonyl; (2) aliphatic urethan protecting groups, such as t-butyloxycarbonyl (BOC), diisopropylmethyl oxycarbonyl, isopropyloxycarbonyl, ethoxycarbonyl, allyloxycarbonyl; and (3) cycloalkyl urethan-type protecting groups, such as cyclopentyloxycarbonyl, adamantyloxycarbonyl,and cyclohexyloxycarbonyl. The preferred alpha-amino protecting group is BOC, even when an $N^\alpha$Me-substituted residue is employed in the 1-position; of course $X^1$ is H when B is desamino.

X is hydrogen or a protecting group for the imidazole nitrogen of His, such as Tos.

$X^2$ may be a suitable protecting group for the phenolic hydroxyl group of Tyr, such as tetrahydropyranyl, tert-butyl, trityl, Bzl, CBZ, 4Br-CBZ and 2,6-dichlorobenzyl(DCB). The preferred protecting group is 2,6-dichlorobenzyl. $X^2$ can be hydrogen which means that there is no side-chain protecting group on the amino acid residue in that position.

$X^3$ is hydrogen or a suitable ester-forming protecting group for the carboxyl group of Asp or Glu, such as benzyl(OBzl), 2,6-dichlorobenzyl, methyl and ethyl.

$X^4$ may be a suitable protecting group for the hydroxyl group of Thr or Ser, such as acetyl, benzoyl, tert-butyl, trityl, tetrahydropyranyl, Bzl, 2,6-dichlorobenzyl and CBZ. The preferred protecting group is Bzl. $X^4$ can be hydrogen, which means there is no protecting group on the hydroxyl group.

$X^5$ is hydrogen or a suitable protecting group for the side chain amido group of Asn or Gln, such as xanthyl(Xan). Asn or Gln is preferably coupled in the presence of hydroxybenzotriazole (HOBt) when $X^5$ is hydrogen.

$X^6$ is a suitable protecting group for the guanido group of Arg, such as nitro, Tos, CBZ, adamantyloxycarbonyl, and BOC, or is hydrogen.

$X^7$ is hydrogen or a suitable protecting group for the side chain amino group of Lys. Illustrative of suitable side chain amino protecting groups are 2-chlorobenzyloxycarbonyl(2-Cl-Z), Tos, t-amyloxycarbonyl and BOC.

$X^8$ is hydrogen or a suitable side-chain protecting group as generally specified above.

Met can optionally be protected by oxygen, but is preferably left unprotected.

The selection of a side chain amino protecting group is not critical except that generally one is chosen which is not removed during deprotection of the alpha-amino groups during the synthesis. However, for some amino acids, e.g. His, protection is not generally necessary after coupling is completed, and the protecting groups may be the same.

$X^9$ is a suitable protecting group for the C-terminal carboxyl group, such as the ester-forming group $X^3$, or is an anchoring bond used in solid-phase synthesis for linking to a solid resin support, or is des-$X^9$, in which case the residue at the C-terminus has a carboxyl moiety which is Y, as defined herein-before. When a solid resin support is used, it may be any of those known in the art, such as one having the formulae: —O—CH$_2$—resin support, —NH—benzhydrylamine (BHA) resin support or —NH—paramethylbenzhydrylamine (MBHA) resin support. When the unsubstituted amide is desired, use of BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 can be used, or should still other groups than the free acid be desired at the C-terminus, it may be preferable to synthesize the peptide using solution synthesis methods as set forth in the Houben-Weyl text.

In the formula for the intermediate, at least one of the X-groups is a protecting group or $X^9$ includes resin support. Thus, the invention also provides a method for manufacturing a peptide of interest by (a) forming an intermediate peptide having at least one protective group and the formula (II): wherein: X, $X^1$, $X^2$, $X^3$, $X^4$, $X^5$, $X^6$, $X^7$ and $X^8$ are each either hydrogen or a protective group and $X^9$ is either a protective group or an anchoring bond to resin support or is des-$X^9$, in which case the residue at the C-terminus may have the desired carboxy moiety; (b) splitting off the protective group or groups or anchoring bond from the peptide of the formula (II); and (c) if desired, converting the resulting peptide of the sequence (I) into a nontoxic salt thereof.

In selecting a particular side chain protecting group to be used in the synthesis of the peptides, the following general rules are followed: (a) the protecting group preferably retains its protecting properties and is not split off under coupling conditions, (b) the protecting group should be stable to the reagent and, with the exception of Xan, is preferably stable under the reaction conditions selected for removing the alpha-amino protecting group at each step of the synthesis, and (c) the side chain protecting group must be removable, upon the completion of the synthesis containing the desired amino acid sequence, under reaction conditions that will not undesirably alter the peptide chain.

The peptides are preferably prepared using solid phase synthesis, such as that generally described by Merrifield, *J. Am. Chem. Soc.*, 85, p 2149 (1963), although other equivalent chemical syntheses known in the art can also be used as previously mentioned. Solid-phase synthesis is commenced from the C-terminus of the peptide by coupling a protected alpha-amino acid to a suitable resin. Such a starting material can be prepared by attaching an alpha-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) 38, 1597-98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1-6. BHA and MBHA resin supports are commercially available and are generally used only when the desired polypeptide being synthesized has an unsubstituted amide at the C-terminal.

To prepare a 29-residue version of the peptide, the C-terminal amino acid, e.g. Arg, protected by BOC and by Tos, can be first coupled to an MBHA resin according to the general procedure set forth in Vale et al. U.S. Pat. No. 4,292,313, using DCCI in DMF and/or CH$_2$Cl$_2$ for 2 hours with stirring. Following the coupling of the BOC-protected amino acid to the resin support, the alpha-amino protecting group is removed, as by using trifluoroacetic acid(TFA) in methylene chloride or TFA alone. The deprotection is carried out at a temperature between about 0° C. and room temperature. Other standard cleaving reagents, such as HCl in dioxane, and conditions for removal of specific alpha-amino protecting groups may be used as described in Schroder & Lubke, "The Peptides", 1, pp 72-75 (Academic Press 1965).

After removal of the alpha-amino protecting group, the remaining alpha-amino- and side-chain-protected amino acids are coupled stepwise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke supra, in Chapter III and by Kapoor, *J. Phar. Sci.*, 59, pp 1-27 (1970). P-nitrophenyl ester(ONp) may also be used to activate the carboxyl end of Asn or Gln for coupling. For example, BOC-Asn(ONp) can be coupled overnight using one equivalent of HOBt in a 50% mixture of DMF and methylene chloride, in which case no DCCI is added.

Each protected amino acid or amino acid sequence is introduced into the solid phase reactor in about a four-fold or more excess, and the coupling may be carried out in a medium of dimethylformamide(DMF):$CH_2Cl_2$ (1:1) or in DMF or $CH_2Cl_2$ alone. In cases where incomplete coupling occurs, the coupling procedure is repeated before removal of the alpha-amino protecting group prior to the coupling of the next amino acid. The success of the coupling reaction at each stage of the synthesis, if performed manually, is preferably monitored by the ninhydrin reaction, as described by E. Kaiser et al., *Anal. Biochem.* 34, 595 (1970). The coupling reactions can be performed automatically, as on a Beckman 990 automatic synthesizer, using a program such as that reported in Rivier et al. *Biopolymers.* 1978, 17, pp 1927–1938.

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups $X$, $X^2$, $X^3$, $X^4$, $X_5$, $X^6$, $X^7$ and $X^8$ and the anchoring bond $X^9$ and also the alpha-amino protecting group $X^1$ if one is used, to obtain the peptide in the form of the free acid. If Met is present in the sequence, the BOC protecting group is preferably first removed using trifluoroacetic acid(TFA)/ethanedithiol prior to cleaving the peptide from the resin with HF to eliminate potential S-alkylation. When using hydrogen fluoride for cleaving, anisole and methylethyl sulfide are included as scavengers in the reaction vessel.

The following Example 1 sets forth a preferred method for synthesizing peptides by the solid-phase technique. It will of course be appreciated that the synthesis of a correspondingly longer peptide is effected in the same manner by merely adding the requisite number of amino acids at the C-terminus of the chain. It is presently felt that biologically active fragments should contain the indicated sequence at the N-terminus because addition of residues to the N-terminus is not considered advantageous.

EXAMPLE 1

The synthesis of the peptide [$Ala^8$, $Nle^{27}$]-hGRF(1-29)-$NH_2$, which has the formula: (SEQ ID NO:3) Tyr-Ala-Asp-Ala-Ile-Phe-Thr-Ala-Ser-Tyr-Arg-Lys-Val-Leu-Gly-Gln-Leu-Ser-Ala-Arg-Lys-Leu-Leu-Gln-Asp-Ile-Xaa-Ser-Arg where Xaa is Nle and the C-terminus is amidated, is conducted in a stepwise manner using a Beckman 990 peptide synthesizer on a commercially available MBHA resin as generally described in Vale et al. U.S. Pat. No. 4,292,313. Coupling of BOC-Arg(Tos) to the resin results in the substitution of about 0.35 mmol. Arg per gram of resin.

After deblocking and neutralization, the peptide chain is built step-by-step on the resin. Deblocking, neutralization and addition of each amino acid is performed in general accordance with the procedure set forth in detail in Rivier, J., *J. Amer. Chem. Soc.*, 96, 2986–2992 (1974). All solvents that are used are carefully degassed by sparging with an inert gas, e.g. helium or nitrogen, to insure the absence of oxygen that might undesirably oxidize the sulfur of the Met residue.

Deblocking is preferably carried out in accordance with Schedule A which follows:

| SCHEDULE A | |
|---|---|
| Reagent | Mixing time (Min.) |
| 1. 60% TFA/2% ethanedithiol | 10 |
| 2. 60% TFA/2% ethanedithiol | 15 |
| 3. IPA/1% ethanedithiol | 0.5 |
| 4. $Et_3N$ (10%) in $CH_2Cl_2$ | 0.5 |
| 5. MeOH | 0.5 |
| 6. $Et_3N$ (10%) in $CH_2Cl_2$ | 0.5 |
| 7. MeOH (twice) | 0.5 |
| 8. $CH_2Cl_2$ (twice) | 0.5 |

The couplings are preferably carried out as set out in Schedule B which follows:

| SCHEDULE B | |
|---|---|
| Reagent | Mixing time (Min.) |
| 9. DCCI | — |
| 10. Boc-amino acid | 50–90 |
| 11. MeOH (twice) | 0.5 |
| 12. $CH_2Cl_2$ (twice) | 0.5 |
| 13. $Ac_2O$ (3M) in $CH_2Cl_2$ | 15.0 |
| 14. $CH_2Cl_2$ | 0.5 |
| 15. MeOH | 0.5 |
| 16. $CH_2Cl_2$ (twice) | 0.5 |

Briefly, one to two mmol. of BOC-protected amino acid in methylene chloride is used per gram of resin, plus one equivalent of 1.0 molar DCCI in methylene chloride for two hours. When BOC-Arg(Tos) is being coupled, a mixture of 50% DMF and methylene chloride is used. Bzl ether is used as the hydroxyl side-chain protecting group for Ser and Thr. The amido group of Asn or Gln may be protected by Xan; however, it is preferably coupled in the presence of 1 eq. of DCCI and 2 eq. of HOBt. 2-chloro-benzyloxycarbonyl(2Cl-Z) is used as the protecting group for the Lys side chain. Tos is used to protect the guanido group of Arg and the imidazole nitrogen of His, and the Glu or Asp side-chain carboxyl group is protected with OBzl. The phenolic hydroxyl group of Tyr is protected with 2,6-dichlorobenzyl(DCB). At the end of the synthesis, the following composition is obtained: BOC-Tyr($X^2$)-Ala-Asp($X^3$)-Ala-Ile-Phe-Thr($X^4$)-Ala-Ser($X^4$)-Tyr($X^2$)-Arg($X^6$)-Lys($X^7$)-Val-Leu-Gly-Gln-Leu-Ser ($X^4$)-Ala-Arg($X^6$)-Lys($X^7$)-Leu-Leu-Gln-Asp(Xa)-Ile-Nle-Ser($X^4$)-Arg($X^6$)-$X^9$ wherein $X^2$ is DCB, $X^3$ is OBzl, $X^4$ is Bzl, $X^6$ is Tos, $X^7$ is 2Cl-Z and $X^9$ is NH-MBHA-resin support.

In order to cleave and deprotect the protected peptide-resin, it is treated with 1.5 ml. anisole, 0.5 ml. methylethylsulfide and 15 ml. hydrogen fluoride(HF) per gram of peptide-resin, at −20° C. for one-half hour and at 0° C. for one-half hour. After elimination of the HF under high vacuum, the resin-peptide remainder is washed alternately with dry diethyl ether and chloroform, and the peptide is then extracted with degassed 2N aqueous acetic acid and separated from the resin by filtration, and lyophilized.

The cleaved, deprotected and lyophilized peptide is then purified by preparative or semi-preparative HPLC as described in Rivier et al., *Peptides: Structure and Biological Function*, (1979) pp 125–8 and Marki et al. *J. Am. Chem. Soc.* 103, 3178 (1981). Cartridges fitting, Waters Associates prep LC-500 are packed with $C_{18}$ Silica from Vydac (300A). A gradient of $CH_3CN$ in triethylammonium phosphate (TEAP) is generated by a low pressure Eldex gradient maker, as described in Rivier, J., *J. Liq. Chromatography* 1, 343–367 (1978). The chromatographic fractions are carefully monitored by HPLC, and only the fractions showing substantial purity are pooled. Desalting of the purified fractions, independently checked for purity, is achieved using a gradient of $CH_3CN$ in 0.1% TFA. The center cut is then lyophilized to yield the desired peptide, the purity of which is measured and found to be greater than about 95%. Purity is further confirmed by mass spectroscopy (MS) and capillary zone electrophoresis.

The optical rotation of the purified peptide is measured using a Perkin-Elmer polarimeter and found to be $[\alpha]_D = -61° \pm 1$ (c=1, 1% acetic acid).

EXAMPLE 2

The synthesis of the 29-residue amidated peptide [Ala$^{16}$, Nle$^{27}$]-hGRF(1-29)-NH$_2$, which has the formula: (SEQ ID NO:4) Tyr-Ala-Asp-Ala-Ile-phe-Thr-Asn-Ser-Tyr-Arg-Lys-Val-Leu-Gly-Ala-Leu-Ser-Ala-Arg-Lys-L eu-Gln-Asp-Ile-Xaa-Ser-Arg, where Xaa is Nle and the C-terminus is amidated, is conducted in a stepwise manner on an MBHA resin using a Beckman 990 Peptide Synthesizer, generally as in Example 1. The peptide is judged to be substantially pure using MS, HPLC and capillary zone electrophoresis.

The optical rotation of the purified peptide is measured using a Perkin-Elmer polarimeter and found to be $[\alpha]_D - 66° \pm 1$ (c=1, 1% acetic acid).

EXAMPLE 3

The synthesis of the 29-residue amidated peptide [Ala$^{24}$, Nle$^{27}$]-hGRF(1-29)-NH$_2$, which has the formula: (SEQ ID NO:5) Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Ala-Asp-Ile-Xaa-Ser-Arg, where Xaa is Nle and the C-terminus is amidated, is conducted in a stepwise manner on an MBHA resin using a Beckman 990 Peptide Synthesizer, generally as in Example 1. The peptide is judged to be substantially pure using MS, HPLC and capillary zone electrophoresis.

The optical rotation of the purified peptide is measured using a Perkin-Elmer polarimeter and found to be $[\alpha] = -67° \pm 1$ (c=1, 1% acetic acid).

EXAMPLE 4

The synthesis of the 29-residue amidated peptide [Ala$^{25}$, Nle$^{27}$]-hGRF(1-29)-NH$_2$, Which has the formula: (SEQ ID NO:6) Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Ala-Ile-Xaa-Ser-Arg, where Xaa is Nle and the C-terminus is amidated, is conducted in a stepwise manner on an MBHA resin using a Beckman 990 Peptide Synthesizer, generally as in Example 1. The peptide is judged to be substantially pure using MS, HPLC and capillary zone electrophoresis.

The optical rotation of the purified peptide is measured using a Perkin-Elmer polarimeter and found to be $[\alpha]_D = -64° \pm 1$ (c=1, 1% acetic acid).

EXAMPLE 5

The synthesis of the 29-residue amidated peptide [Ala$^{8,16}$, Nle$^{27}$]-hGRF(1-29)-NH$_2$, which has the formula: (SEQ ID NO:7) Tyr-Ala-Asp-Ala-Ile-Phe-Thr-Ala-Ser-Tyr-Arg-Lys-Val-Leu-Gly-Ala-Leu-Ser-Ala-Arg-Lys-Leu-Leu-Gln-Asp-Ile-Xaa-Ser-Arg, where Xaa is Nle and the C-terminus is amidated, is conducted in a stepwise manner on an MBHA resin using a Beckman 990 Peptide Synthesizer, generally as in Example 1. The peptide is judged to be substantially pure using MS, HPLC and capillary zone electrophoresis.

EXAMPLE 6

The synthesis of the 29-residue amidated peptide [NCH$_3$Tyr$^1$, Ala$^{8,9,15,22,28}$, Nle$^{27}$]-hGRF(1-29)-NH$_2$, which has the formula: (SEQ ID NO:8) Tyr-Ala-Asp-Ala-Ile-Phe-Thr-Ala-Ala-Tyr-Arg-Lys-Val-Leu-Ala-Gln-Leu-Ser-Ala-Arg-Lys-Ala-Leu-Gln-Asp-Ile-Xaa-Ala-Arg, where the N-terminus is substituted by N-methyl, Xaa is Nle and the C-terminus is amidated, is conducted in a stepwise manner on an MBHA resin using a Beckman 990 Peptide Synthesizer, generally as in Example 1. The peptide is judged to be substantially pure using MS, HPLC and capillary zone electrophoresis.

The optical rotation of the purified peptide is measured using a Perkin-Elmer polarimeter and found to be $[\alpha]_D = -57° \pm 1$ (c=1, 1% acetic acid).

EXAMPLE 7

The synthesis of a 29-residue amidated peptide [Ala$^{8,25}$, Nle$^{27}$]-hGRF(1-29)-NH$_2$ having the formula: (SEQ ID NO:9) Tyr-Ala-Asp-Ala-Ile-Phe-Thr-Ala-Ser-Tyr-Arg-Lys-Val-Leu-Gly-Gln-Leu-Ser-Ala-Arg-Lys-Leu-Leu-Gln-Ala-Ile-Xaa-Ser-Arg, where Xaa is Nle and the C-terminus is amidated, is conducted in a stepwise manner on an MBHA resin using a Beckman 990 Peptide Synthesizer, generally as in Example 1. The peptide is judged to be substantially pure using MS, HPLC and capillary zone electrophoresis.

EXAMPLE 8

The synthesis of a 29-residue amidated peptide [Ala$^{8,16,24}$, Nle$^{27}$]-hGRF(1-29)-NH$_2$ having the formula: (SEQ ID NO:10) Tyr-Aaa-Asp-Ala-Ile-Phe-Thr-Ala-Ser-Tyr-Arg-Lys-Val-Leu-Gly-Ala-Leu-Ser-Ala-Arg-Lys-Leu-Leu-Ala-Asp-Ile-Xaa-Ser-Arg, where Xaa is Nle and the C-terminus is amidated, is conducted in a stepwise manner on an MBHA resin using a Beckman 990 Peptide Synthesizer, generally as in Example 1. The peptide is judged to be substantially pure using MS, HPLC and capillary zone electrophoresis.

EXAMPLE 9

The synthesis of a 29-residue amidated peptide [Ala$^{8,16,25}$, Nle$^{27}$]-hGRF(1-29)-NH$_2$ having the formula: (SEQ ID NO:11) Tyr-Ala-Asp-Ala-Ile-Phe-Thr-Ala-Ser-Tyr-Arg-Lys-Val-Leu-Gly-Ala-Leu-Ser-Ala-Arg-Lys-Leu-Leu-Gln-Ala-Ile-Xaa-Ser-Arg, where Xaa is Nle and the C-terminus is amidated, is conducted in a stepwise manner on an MBHA resin using a Beckman 990 Peptide Synthesizer, generally as in Example 1. The peptide is judged to be substantially pure using MS, HPLC and capillary zone electrophoresis.

EXAMPLE 10

The synthesis of a 29-residue amidated peptide [Ala$^{8,16,24,25}$, Nle$^{27}$]-hGRF(1-29)-NH$_2$ having the formula: (SEQ ID NO:12) Tyr-Ala-Asp-Ala-Ile-Phe-Thr-Ala-Ser-Tyr-Arg-Lys-Val-Leu-Gly-Ala-Leu-Ser-Ala-Arg-Lys-Leu-Leu-Ala-Ala-Ile-Xaa-Ser-Arg, where Xaa is Nle and the C-terminus is amidated, is conducted in a stepwise manner on an MBHA resin using a Beckman 990 Peptide Synthesizer, generally as in Example 1. The peptide is judged to be substantially pure using MS, HPLC and capillary zone electrophoresis.

EXAMPLE 11

The synthesis of a 29-residue amidated peptide [Ala$^{16,24,25}$, Nle$^{27}$]-hGRF(1-29)-NH$_2$ having the formula: (SEQ ID NO:13) Tyr-Ala-Asp-Ala-Ile-Phe-Thr-Asn-Ser-Tyr-Arg-Lys-Val-Leu-Gly-Ala-Leu-Ser-Ala-Arg-Lys-Leu-Leu-Gln-Asp-Ile-Xaa-Ser-Arg, where Xaa is Nle and the C-terminus is amidated, is conducted in a stepwise manner on an MBHA resin using a Beckman 990 Peptid Synthesizer, generally as in Example 1. The peptide is judged to be substantially pure using MS, HPLC and capillary zone electrophoresis.

EXAMPLE 12

The synthesis of a 40-residue amidated peptide [C$^\alpha$MeHis$^1$, D-NMA$^2$, Ala$^8$, CML$^{27}$]-hGRF(1-40)-NH$_2$ is conducted in a stepwise manner using a Beckman 990 Peptide Synthesizer on an MBHA resin as generally descried in Vale et al. U.S. Pat. No. 4,292,313.

EXAMPLE 13

The synthesis of [D-NMA$^2$, Aib$^{16}$, CML$^{27}$]-rGRF(1-43)-OH is conducted in a stepwise manner using a Beckman 990 Peptide Synthesizer, using a chloromethylated resin with initial coupling as described in *Chemistry Letters, supra*, and thereafter in the manner generally described in Example 1.

EXAMPLE 14

The synthesis of the hGRF analog [NMeTyr$^1$, Lys$^8$, Ala$^{15,24}$, CML$^{27}$, Asn$^{28}$]-hGRF(1-29)-NH$_2$ is conducted in a stepwise manner using a Beckman 990 Peptide Synthesizer on an MBHA resin as in Example 1.

EXAMPLE 15

The synthesis of the hGRF analog [NMeTyr$^1$, Ala$^{16}$, D-Lys$^{21}$, CML$^{27}$]-hGRF(1-29)-NH$_2$ is conducted in a stepwise manner using a Beckman 990 Peptide Synthesizer on an MBHA resin as in Example 1.

EXAMPLE 16

The synthesis of [NMeHis$^1$, D-NMA$^2$, Aib$^8$, D-Arg$^{21}$, CML$^{27}$]-rGRF(1-29)-NH$_2$, is conducted in a stepwise manner using a Beckman 990 Peptide Synthesizer on an MBHA resin as in Example 1.

EXAMPLE 17

The synthesis of [NMeTyr$^1$, Ala$^8$, C$^\alpha$Me-D-Tyr$^{10}$, D-Lys$^{21}$, CML$^{27}$]-hGRF(1-29)-NH$_2$ is conducted in a stepwise manner using a Beckman 990 Peptide Synthesizer on an MBHA resin as in Example 1.

EXAMPLE 18

The synthesis of [D-NMA$^2$, CML$^5$, D-Lys$^{21}$, Ala$^{25}$, Nva$^{27}$]-rGRF(1-29)-NH$_2$ is conducted in a stepwise manner using a Beckman 990 Peptide Synthesizer on an MBHA resin as in Example 1.

EXAMPLE 19

The synthesis of [D-Phe$^1$, D-NMA$^2$, Glu$^8$, C$^\alpha$Me-Tyr$^{10}$, Ile$^{13}$, Ala$^{16}$, CML$^{22}$]-hGRF(1-32)-NHCH$_2$CH$_3$ is conducted in a stepwise manner using a Beckman 990 Peptide Synthesizer using the same general procedure as described in Example 1 but employing an N-ethylaminomethyl resin as generally described in Kornreich et al. U.S. Pat. No. 4,569,967.

EXAMPLE 20

The synthesis of [pCl-Phe$^1$, D-NMA$^2$, CMA$^{19}$, Val$^{22}$, Aib$^{25}$, Ile$^{27}$]-rGRF(1-29)-NH$_2$ is conducted in a stepwise manner using a Beckman 990 Peptide Synthesizer on an MBHA resin, in the manner generally described in Example 1.

EXAMPLE 21

The synthesis of [CML$^1$, D-NMA$^2$, D-Asp$^3$, Lys$^8$, Ala$^{16}$, CMA$^{22}$]-hGRF(1-32)-NH$_2$ is conducted in a stepwise manner using a Beckman 990 Peptide Synthesizer on an MBHA resin as in Example 1.

EXAMPLE 22

The synthesis of [D-Tyr$^1$, D-NMA$^2$, D-Asp$^3$, C$^\alpha$Me-D-Tyr$^{10}$, Ala$^{15,24}$, D-Arg$^{21}$, CML$^{22}$, D-Met$^{27}$]-hGRF(1-29)-NH$_2$ is conducted in a stepwise manner using a Beckman 990 Peptide Synthesizer on an MBHA resin as in Example 1.

EXAMPLE 23

The synthesis of [D-His$^1$, D-NMA$^2$, Ala$^{8,27}$, CML$^{13}$]-rGRF(1-29)-NH$_2$ is conducted in a stepwise manner using a Beckman 990 Peptide Synthesizer on an MBHA resin, in the manner generally described in Example 1.

EXAMPLE 24

The synthesis of an rGRF analog fragment i.e. [NMeTyr$^1$, D-NMA$^2$, Glu$^8$, CMA$^{13}$, Aib$^{16}$, D-Arg$^{21}$, C$^\alpha$MeIle$^{22}$]-rGRF(1-29)-NH$_2$ is conducted in a stepwise manner using a Beckman 990 Peptide Synthesizer on an MBHA resin as in Example 1.

EXAMPLE 25

The synthesis of [CML$^1$, D-NMA$^2$, Leu$^{13}$, Ala$^{16,27}$, CMA$^{19,22}$]-rGRF-(1-29)-NH$_2$ is conducted in a stepwise manner using a Beckman 990 Peptide Synthesizer on an MBHA resin as in Example 1.

EXAMPLE 26

The synthesis of [C$^\alpha$MePhe$^1$, NMA$^2$, Lys$^8$, Arg$^{12}$, Ile$^{13,27}$, CMA$^{19}$, Ala$^{24}$]-hGRF(1-29)-NH$_2$ is conducted in a stepwise manner using a Beckman 990 Peptide Synthesizer on an MBHA resin as generally described in Vale et al. U.S. Pat. No. 4,292,313.

EXAMPLE 27

The synthesis of [desaminoD-Tyr$^1$, D-NMA$^2$, Aib$^8$, Phe$^{10}$, C$^\alpha$MeVal$^{13}$, Leu$^{27}$, Asn$^{28}$]-hGRF(1-29)-NH$_2$ is conducted in a stepwise manner using a Beckman 990 Peptide Synthesizer on an MBHA resin as generally described in Vale et al. U.S. Pat. No. 4,292,313.

EXAMPLE 28

The synthesis of [D-NMA$^2$, C$^\alpha$MeTyr$^{10}$, C$^\alpha$MeVal$^{13}$, Ala$^{16}$, CML$^{22}$, Nle$^{27}$, Asn$^{28}$]-hGRF(1-29)-NH$_2$ is conducted in a stepwise manner using a Beckman 990 Peptide Synthesizer on an MBHA resin as generally described in Vale et al. U.S. Pat. No. 4,292,313.

EXAMPLE 29

The synthesis of [C$^\alpha$MePhe$^1$, D-NMA$^2$, Ala$^8$, C$^\alpha$Me-Tyr$^{10}$, C$^\alpha$MeIle$^{13}$, Val$^{27}$]-rGRF(1-29)-NH$_2$ is conducted in a stepwise manner using a Beckman 990 Peptide Synthesizer on an MBHA resin as in Example 1.

EXAMPLE 30

The synthesis of [desaminoD-Met$^1$, D-NMA$^2$, C$^\alpha$MeTyr$^{10}$, C$^\alpha$MeVal$^{13}$, CMA$^{19}$, Ala$^{24}$, Asn$^{28}$]-hGRF(1-44)-NH$_2$ is conducted in a stepwise manner using a Beckman 990 Peptide Synthesizer on an MBHA resin as generally described in Vale et al. U.S. Pat. No. 4,292,313.

EXAMPLE 31

The synthesis of [NMeHis$^1$, D-NMa$^2$, Aib$^8$, C$^\alpha$MeVal$^{13}$, Nle$^{27}$]-hGRF(1-29)-NH$_2$ is conducted in a stepwise manner using a Beckman 990 Peptide Synthesizer on an MBHA resin as generally described in Vale et al. U.S. Pat. No. 4,292,313.

EXAMPLE 32

The synthesis of [NMeTyr$^1$, Ala$^{15,16}$, CML$^{26}$, Nle$^{27}$, Asn$^{28}$]-hGRF(1-29)-NH$_2$ is conducted in a stepwise manner using a Beckman 990 Peptide Synthesizer on an MBHA resin as in Example 1.

EXAMPLE 33

The synthesis of [NMeTyr$^1$, Ala$^{8,15,28}$, CML$^{23}$, Nle27]-hGRF(1-29)-NH$_2$ is conducted in a stepwise manner using a Beckman 990 Peptide Synthesizer on an MBHA resin as in Example 1.

EXAMPLE 34

The synthesis of [NMeTyr$^1$, CML$^{13}$, Ala$^{15,24}$, Nle$^{27}$, Asn$^{28}$]-hGRF(1-29)-NH$_2$ is conducted in a stepwise manner using a Beckman 990 Peptide Synthesizer on an MBHA resin as in Example 1.

EXAMPLE 35

The synthesis of [NMeTyr$^1$, Ala$^{9,15}$, Aib$^{25}$, Nle$^{27}$, Asn$^{28}$]-hGRF(1-29)-NH$_2$ is conducted in a stepwise manner using a Beckman 990 Peptide Synthesizer on an MBHA resin as in Example 1.

EXAMPLE 36

The synthesis of [NMeTyr$^1$, Ala$^{15,16}$, CML$^{17}$, Nle$^{27}$, Aib$^{28}$]-hGRF(1-29)-NH$_2$ is conducted in a stepwise manner using a Beckman 990 Peptide Synthesizer on an MBHA resin as in Example 1.

EXAMPLE 37

The synthesis of [NMeTyr$^1$, Ala$^{8,15}$, CML$^{22}$, Nle$^{27}$, Asn$^{28}$]-hGRF(1-29)-NH$_2$ is conducted in a stepwise manner using a Beckman 990 Peptide Synthesizer on an MBHA resin as in Example 1.

EXAMPLE 38

The synthesis of [NMeTyr$^1$, Aib$^{8,9,15}$, Ala$^{15}$, Nle$^{27}$, Asn$^{28}$]-hGRF(1-29)-NH$_2$ is conducted in a stepwise manner using a Beckman 990 Peptide Synthesizer on an MBHA resin as in Example 1.

EXAMPLE 39

The synthesis of [NMeTyr$^1$, CML$^5$, Ala$^{15,16}$, Nle$^{27}$, Asn$^{28}$]-hGRF(1-29)-NH$_2$ is conducted in a stepwise manner using a Beckman 990 Peptide Synthesizer on an MBHA resin as in Example 1.

EXAMPLE 40

The synthesis of [NMeTyr$^1$, Ala$^{8,15,16,24,25}$, Nle$^{27}$, Asn$^{28}$]-hGRF(1-29)-NH$_2$ is conducted in a stepwise manner using a Beckman 990 Peptide Synthesizer on an MBHA resin as in Example 1.

EXAMPLE 41

The synthesis of [NMeTyr$^1$, Ala$^{8,15,16,24}$, Nle$^{27}$, Asn$^{28}$]-hGRF(1-29)-NH$_2$ is conducted in a stepwise manner using a Beckman 990 Peptide Synthesizer on an MBHA resin as in Example 1.

EXAMPLE 42

The synthesis of [NMeTyr$^1$, Ala$^{8,15,16}$, Nle$^{27}$, Asn$^{28}$]-hGRF(1-29)-NH$_2$ is conducted in a stepwise manner using a Beckman 990 Peptide Synthesizer on an MBHA resin as in Example 1.

To determine the relative effectiveness of synthetic peptides to promote the release of growth hormone, in vitro assays are carried out using synthetic hpGRF(1-40)-OH as a standard in side-by-side comparison with equimolar concentrations of the representative analogs which have been synthesized. Cultures are used which include cells of rat pituitary glands removed some three to five days previously. Such cultures are considered optimal for the secretion of growth hormone and are used for the comparative testing, in the general manner described in Vale et al. *Endocrinology*, 91, 562–572 (1972) and as more particularly described in Vale et al. *Endocrinology*, 112, 1553–1555 (1983). Incubation with the substance to be tested is carried out for 3 to 4 hours, and aliquots of the culture medium are removed and processed to measure their contents in immunoreactive GH(ir GH) by a well-characterized radioimmunoassay.

The synthetic peptides prepared in the Examples can be compared with synthetic hpGRF(1-40)-OH in in vitro assays. All are considered to exhibit generally greater potencies for the secretion of GH and similar intrinsic activities. All of these synthetic peptides are considered to be biologically active and potentially useful for stimulating the release of GH by the pituitary.

The results of such comparative testing for equimolar concentrations of certain of these peptides are shown in Table I.

TABLE 1

| Peptide | In Vitro Potencies |
| --- | --- |
| hGRF(1-40)-OH (standard for this test) | 1.0 |
| Example No. 1 (SEQ ID NO: 3) | 2.143(1.178–4.065) |
| Example No. 2 (SEQ ID NO: 4) | 1.502(0.727–2.859) |
| Example No. 3 (SEQ ID NO: 5) | 1.345(0.595–2.068) |
| Example No. 4 (SEQ ID NO: 6) | 1.34(0.837–2.190) |

In addition to the in vitro tests for secretion of growth hormone, in vivo experiments inject the synthetic peptides intravenously into urethane-anesthetized male rats and determine that they suppress spontaneous GH secretion without abolishing the response to exogenous GRF. Blood samples are taken immediately prior to, and 10, 30 and 60 minutes after injections, and GH levels in blood are measured by radioimmunoassay. This in vivo testing of these synthetic peptides shows that each has greater biological potency than that exhibited by hpGRF(1-40)-OH and has substantially longer duration of effectiveness, which is shown in blood levels of pituitary GH when measured at both 30 and 60 min. after IV injection. Other known GRF in vivo tests that are known to be effective to detect secretion of GH are used to confirm these results. Dosages between about 500 nanograms and about 50 micrograms of these peptides per Kg. of body weight are considered to be effective in causing GH secretion.

Such synthetic hGRF analogs and possibly rGRF analogs are considered to be useful for human applications in which a physician wishes to elevate GH production. Stimulation of GH secretion by such analogs is of interest in patients with complete or relative GH deficiency caused by underproduction of endogenous GRF. Furthermore, it is probable that increased GH secretion and its attendant increase in growth could be obtained in humans or animals with normal GH levels. Moreover, administration should alter body fat content and modify other GH-dependent metabolic, immunologic and developmental processes. For example, these analogs may be useful as a means of stimulating anabolic processes in human beings under circumstances such as following the incurring of burns. As another example, these analogs may be administered to commercial warm-blooded animals, such as chickens, turkeys, pigs, goats, cattle and sheep, and may be used in aquiculture for raising fish and other cold-blooded marine animals, e.g. sea turtles and eels, and amphibians, to accelerate growth and increase the ratio of protein to fat gained by feeding effective amounts of the peptides.

For administration to humans, these synthetic peptides should have a purity of at least about 93% and preferably at least 98%. Purity, for purposes of this application, refers to the intended peptide constituting the stated weight % of all peptides and peptide fragments present. For the administration of such synthetic peptides to commercial and other animals in order to promote growth and reduce fat content, lower purities may be acceptable.

These synthetic peptides or the nontoxic salts thereof, combined with a pharmaceutically or veterinarily acceptable carrier to form a pharmaceutical composition, may be administered to animals, including humans, either intravenously, subcutaneously, intramuscularly, percutaneously, e.g. intranasally or even orally. The administration may be employed by a physician to stimulate the release of GH where the host being treated requires such therapeutic treatment. The required dosage will vary with the particular condition being treated, with the severity of the condition and with the duration of desired treatment.

Such peptides are often administered in the form of nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be orally administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered to humans under the guidance of a physician, and pharmaceutical compositions will usually contain the peptide in conjunction with a conventional, solid or liquid, pharmaceutically-acceptable carrier. Usually, the parenteral dosage will be from about 0.01 to about 1 microgram of the peptide per kilogram of the body weight of the host.

It may also be desirable to deliver such a peptide over prolonged periods of time, for example, for periods of one week to one year from a single administration, and slow release, depot or implant dosage forms may be utilized. For example, a dosage form may contain a pharmaceutically acceptable non-toxic salt of the compound which has a low degree of solubility in body fluids, for example, an acid addition salt with the polybasic acid; a salt with a polyvalent metal cation; or combination of the two salts. A relatively insoluble salt may also be formulated in a gel, for example, an aluminum stearate gel. A suitable slow release depot formulation for injection may also contain the peptide or a salt thereof dispersed or encapsulated in a slow degrading, non-toxic or non-antigenic polymer, such as a polylactic acid/polyglycolic acid polymer, for example, as described in U.S. Pat. No. 3,773,919. These compounds may also be formulated into silastic implants.

It is also possible to administer the peptides transdermally to humans over an extended period of time using electrical current, as reported in Meyer, B.R. et al., *Clin. Pharm. & Therapeutics*, 44, 6, 607-612 (1988). For example, transdermal patches can be used which utilize a 9-volt battery to continuously apply about 0.2 milliamp current to human skin and which hereby effectively deliver the peptides through the epidermis into the bloodstream.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, modifications in the peptide chain, particularly deletions beginning at the carboxyl terminus of the peptide and extending to about position-29, can be made in accordance with the known experimental practises to date to create peptides or peptide fragments that retain all or very substantial portions of the biological potency of the peptide, and such peptides are considered as being within the scope of the invention. Moreover, additions may be made to either terminus, or to both terminals, and/or generally equivalent residues can be substituted for naturally occurring residues, as is well-known in the overall art of peptide chemistry, to produce other analogs having at least a substantial portion of the potency of the claimed polypeptide without deviating from the scope of the invention. Moreover, modifications may be made to the preferred —NH$_2$ group at the C-terminus in accordance with the state of this art today; for example, the carboxyl moiety of the amino acid residue at the C-terminus can be the radical —COOR,—CRO,—CONHNHR,—CON(R)(R') or —CH$_2$OR, with R and R' being lower alkyl, fluoro lower alkyl or hydrogen, without deviating from the invention, for such modifications result in equivalent synthetic peptides.

Various features of the invention are emphasized in the claims which follow.

What is claimed is:

1. A synthetic peptide, or a nontoxic salt thereof, having the formula SEQ ID NO:16 wherein B is present at the N-terminus; Xaa$_1$ is Tyr or D-Tyr; B is H or N$^\alpha$Me; Xaa$_8$ is Ala, Aib or Asn; Xaa$_{15}$ is Gly or Ala; Xaa$_{16}$ is Ala, Aib or Gln; Xaa$_{21}$ is Lys; Xaa$_{24}$ is Ala, Aib or Gln; Xaa$_{25}$ is Ala, Aib or Asp; Xaa$_{27}$ is Nle; Xaa$_{28}$ is Ser or Asn; NHR is present at the C-terminus with R being H or lower alkyl; proivded that at least one of Xaa$_8$, Xaa$_{16}$, Xaa$_{24}$ or Xaa$_{25}$ is Ala or Aib, and that the 3-residue sequence Gln-Gln-Gly can be optionally deleted from the C-terminus.

2. The peptide of claim 1 having SEQ ID NO:3 where Xaa is Nle and the C-terminus is amidated.

3. The peptide of claim 1 having SEQ ID NO:4 where Xaa is Nle and the C-terminus is amidated.

4. The peptide of claim 1 having SEQ ID NO:5 where Xaa is Nle and the C-terminus is amidated.

5. The peptide of claim 1 having SEQ ID NO:6 where Xaa is Nle and the C-terminus is amidated.

6. A synthetic peptide, or a nontoxic salt thereof, having SEQ ID NO:14 wherein B is present at the N-terminus; $Xaa_1$ is Tyr, D-Tyr, Met, Phe, D-Phe, pCl-Phe, Leu, His or D-His; B is H, $C^\alpha Me$, $N^\alpha Me$, desamino, Ac or For; $Xaa_2$ is Ala, D-Ala, NMA or D-NMA; $Xaa_3$ is Asp or D-Asp; $Xaa_5$ is Ile or Leu; $Xaa_8$ is Ala, Aib, Ser or Asn; $Xaa_9$ is Ser, Ala or Aib; $Xaa_{10}$ is Tyr, D-Tyr or Phe; $Xaa_{12}$ is Arg or Lys; $Xaa_{13}$ is Ile, Val, Leu or Ala; $Xaa_{15}$ is Gly or Ala; $Xaa_{16}$ is Ala, Aib or Gln; $Xaa_{18}$ is Ser or Tyr; $Xaa_{21}$ is Lys, D-Lys, Arg or D-Arg; $Xaa_{22}$ is Leu, Ile, Ala, Aib or Val; $Xaa_{24}$ is Ala, Aib, Gln or His; $Xaa_{25}$ is Ala, Aib, Asp or Glu; $Xaa_{26}$ is Ile or Leu; $Xaa_{27}$ is Nle, Met, D-Met, Ala, Ile, Leu, Nva or Val; $Xaa_{28}$ is Asn, Ala, Aib or Ser; $Xaa_{34}$ is Ser or Arg; $Xaa_{38}$ is Arg or Gln; $Xaa_{39}$ is Gly or Arg; $Xaa_{40}$ is Ala or Ser; $Xaa_{42}$ is Phe, Ala or Val; $Xaa_{43}$ is Asn or Arg; $Xaa_{44}$ is Leu or Val; and the C-terminus is amidated; provided however that Ala or Aib is present in at least one of $Xaa_8$, $Xaa_{16}$, $Xaa_{24}$ or $Xaa_{25}$.

7. The peptide of claim 6 wherein $Xaa_{27}$ is Nle and residues 30 through 44 are deleted.

8. The peptide of claim 6 wherein $Xaa_{15}$ is Ala.

9. The peptide of claim 6 wherein $Xaa_{28}$ is Asn.

10. The peptide of claim 6 wherein $Xaa_8$ is Ala.

11. The peptide of claim 6 wherein $Xaa_{16}$ is Ala.

12. The peptide of claim 6 wherein $Xaa_{24}$ is Ala.

13. The peptide of claim 6 wherein $Xaa_{25}$ is Ala.

14. The peptide of claim 6 wherein $Xaa_8$ is Aib.

15. The petpide of claim 6 wherein $Xaa_{16}$ is Aib.

16. The peptide of claim 6 wherein $Xaa_{24}$ is Aib.

17. The peptide of claim 6 wherein $Xaa_{25}$ is Aib.

18. The peptide of claim 6 having SEQ ID NO:8 wherein the N-terminus is substituted by N-methyl, Xaa is NLe, and the C-terminus is amidated.

19. A composition for stimulating the release of GH in an animal comprising a peptide according to claim 6 or a nontoxic salt thereof, and a pharmaceutically or veterinarily acceptable liquid or solid carrier therefor.

20. A synthetic peptide, or a nontoxic salt thereof, having SEQ ID NO:16 wherein B is present at the N-terminus; $Xaa_1$ is Tyr, D-Tyr, Phe, D-Phe, His or D-His; B is H, $C^\alpha Me$ or $N^\alpha Me$; $Xaa_8$ is Ala, Aib or Asn; $Xaa_{15}$ is Gly or Ala; $Xaa_{16}$ is Ala, Aib or Gln; $Xaa_{21}$ is Lys or Arg; $Xaa_{24}$ is Ala, Aib or Gln; $Xaa_{25}$ is Ala, Aib or Asp; $Xaa_{27}$ is Nle; $Xaa_{28}$ is Asn or Ser; NHR is present at the C-terminus with R being H or lower alkyl; provided however that Gly, Gln-Gly or Gln-Gln-Gly may be deleted at the C-terminus, and provided also that at least one of $Xaa_8$, $Xaa_{16}$, $Xaa_{24}$ or $Xaa_{25}$ is Ala or Aib.

* * * * *

UNITED STATES PATENT AND TRADEMARK OFFICE
CERTIFICATE OF CORRECTION

PATENT NO. : 5,262,519
DATED : November 16, 1993
INVENTOR(S) : Rivier, et. al.

It is certified that error appears in the above-indentified patent and that said Letters Patent is hereby <u>TITLE PAGE</u>: On the title page, following the one entry under "Foreign Patent Documents", insert:
-- 9116923 11/1991 PCT Int'l Appl. --
OTHER PUBLICATIONS:

Ling et al., "Synthetic GRF analogs as competitive antagonists of GRF," <u>Therapeutic Agents Produced by Genetic Engineering</u>, "Quo Vadis?" Symposium, Sanofi Group, May 29-30, 1985, Toulouse-Labège, France, pp. 309-322.

Hernandez et al., "Synthesis and biological activity of growth hormone-releasing factor analogs," in <u>Peptides: Chemistry, Structure and Biology</u>, Proceedings of the Eleventh American Peptide Symposium, July 9-14, 1989, La Jolla, California, Rivier, J.E. and Garland, R.M. eds., ESCOM, Leiden, Holland (1990), pp. 236-238.

Cervini et al., "A SAR study of the complete Ala and partial Aib scans of the growth hormone releasing factor: [$Nle^{27}$]hGRF(1-29)-$NH_2$," in <u>Peptides: Chemistry and Biology</u>, Proceedings of the Twelfth American Peptide Symposium, June 16-21, 1991, Cambridge, Massachusetts, Smith, J.A. and Rivier, J.E. eds., ESCOM, Leiden, Holland (1992), pp. 437-438.

UNITED STATES PATENT AND TRADEMARK OFFICE
CERTIFICATE OF CORRECTION

PATENT NO. : 5,262,519
DATED : November 16, 1993
INVENTOR(S) : Rivier, et. al.

It is certified that error appears in the above-indentified patent and that said Letters Patent is hereby corrected as shown below:

Column 24, Claim 1, line 63, change "proivded" to -- provided --. Column 26, Claim 18, line 12, change "NLe" to --Nle--.

Signed and Sealed this

Thirtieth Day of August, 1994

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 44 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:1:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

( 2 ) INFORMATION FOR SEQ ID NO:2:

( i ) SEQUENCE CHARACTERISTICS:
( A ) LENGTH: 43 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:2:

His Ala Asp Ala Ile Phe Thr Ser Ser Tyr Arg Arg Ile Leu Gly Gln
1               5                   10                  15

Leu Tyr Ala Arg Lys Leu Leu His Glu Ile Met Asn Arg Gln Gln Gly
            20                  25                  30

Glu Arg Asn Gln Glu Gln Arg Ser Arg Phe Asn
        35                  40

( 2 ) INFORMATION FOR SEQ ID NO:3:

( i ) SEQUENCE CHARACTERISTICS:
( A ) LENGTH: 29 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:3:

Tyr Ala Asp Ala Ile Phe Thr Ala Ser Tyr Arg Lys Val Leu Gly Gln
1               5                   10                  15

Leu Ser Ala Arg Lys Leu Leu Gln Asp Ile Xaa Ser Arg
            20                  25

( 2 ) INFORMATION FOR SEQ ID NO:4:

( i ) SEQUENCE CHARACTERISTICS:
( A ) LENGTH: 29 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:4:

Tyr Ala Asp Ala Ile Phe Thr Asn Ser Tyr Arg Lys Val Leu Gly Ala

-continued

```
          1               5                    10                        15
      Leu  Ser  Ala  Arg  Lys  Leu  Leu  Gln  Asp  Ile  Xaa  Ser  Arg
                     20                        25
```

( 2 ) INFORMATION FOR SEQ ID NO:5:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:5:

```
      Tyr  Ala  Asp  Ala  Ile  Phe  Thr  Asn  Ser  Tyr  Arg  Lys  Val  Leu  Gly  Gln
      1                   5                        10                        15

Leu  Ser  Ala  Arg  Lys  Leu  Leu  Ala  Asp  Ile  Xaa  Ser  Arg
                     20                        25
```

( 2 ) INFORMATION FOR SEQ ID NO:6:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:6:

```
      Tyr  Ala  Asp  Ala  Ile  Phe  Thr  Asn  Ser  Tyr  Arg  Lys  Val  Leu  Gly  Gln
      1                   5                        10                        15

Leu  Ser  Ala  Arg  Lys  Leu  Leu  Gln  Ala  Ile  Xaa  Ser  Arg
                     20                        25
```

( 2 ) INFORMATION FOR SEQ ID NO:7:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:7:

```
      Tyr  Ala  Asp  Ala  Ile  Phe  Thr  Ala  Ser  Tyr  Arg  Lys  Val  Leu  Gly  Ala
      1                   5                        10                        15

Leu  Ser  Ala  Arg  Lys  Leu  Leu  Gln  Asp  Ile  Xaa  Ser  Arg
                     20                        25
```

( 2 ) INFORMATION FOR SEQ ID NO:8:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:8:

```
      Tyr  Ala  Asp  Ala  Ile  Phe  Thr  Ala  Ala  Tyr  Arg  Lys  Val  Leu  Ala  Gln
      1                   5                        10                        15

Leu  Ser  Ala  Arg  Lys  Ala  Leu  Gln  Asp  Ile  Xaa  Ala  Arg
                     20                        25
```

( 2 ) INFORMATION FOR SEQ ID NO:9:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:9:

Tyr Ala Asp Ala Ile Phe Thr Ala Ser Tyr Arg Lys Val Leu Gly Gln
   1               5                   10                  15
   Leu Ser Ala Arg Lys Leu Leu Gln Ala Ile Xaa Ser Arg
               20                  25

( 2 ) INFORMATION FOR SEQ ID NO:10:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:10:

Tyr Ala Asp Ala Ile Phe Thr Ala Ser Tyr Arg Lys Val Leu Gly Ala
   1               5                   10                  15
   Leu Ser Ala Arg Lys Leu Leu Ala Asp Ile Xaa Ser Arg
               20                  25

( 2 ) INFORMATION FOR SEQ ID NO:11:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:11:

Tyr Ala Asp Ala Ile Phe Thr Ala Ser Tyr Arg Lys Val Leu Gly Ala
   1               5                   10                  15
   Leu Ser Ala Arg Lys Leu Leu Gln Ala Ile Xaa Ser Arg
               20                  25

( 2 ) INFORMATION FOR SEQ ID NO:12:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:12:

Tyr Ala Asp Ala Ile Phe Thr Ala Ser Tyr Arg Lys Val Leu Gly Ala
   1               5                   10                  15
   Leu Ser Ala Arg Lys Leu Leu Ala Ala Ile Xaa Ser Arg
               20                  25

( 2 ) INFORMATION FOR SEQ ID NO:13:

( i ) SEQUENCE CHARACTERISTICS:
      ( A ) LENGTH: 29 amino acids
      ( B ) TYPE: amino acid
      ( C ) STRANDEDNESS: single (D) TOPOLOGY: unknown (ii) MOLECULE TYPE: peptide (xi) SEQUENCE DESCRIPTION: SEQ ID NO:13:

Tyr Ala Asp Ala Ile Phe Thr Asn Ser Tyr Arg Lys Val Leu Gly Ala
1               5                   10                  15
Leu Ser Ala Arg Lys Leu Leu Gln Asp Ile Xaa Ser Arg
            20                  25

(2) INFORMATION FOR SEQ ID NO:14:

(i) SEQUENCE CHARACTERISTICS:
    (A) LENGTH: 44 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:14:

Xaa Xaa Xaa Ala Xaa Phe Thr Xaa Xaa Xaa Arg Xaa Xaa Leu Xaa Xaa
1               5                   10                  15
Leu Xaa Ala Arg Xaa Xaa Leu Xaa Xaa Xaa Xaa Xaa Arg Gln Gln Gly
            20                  25                  30
Glu Xaa Asn Gln Glu Xaa Xaa Xaa Arg Xaa Xaa Xaa
            35                  40

(2) INFORMATION FOR SEQ ID NO:15:

(i) SEQUENCE CHARACTERISTICS:
    (A) LENGTH: 29 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:15:

Xaa Xaa Xaa Ala Ile Phe Thr Xaa Ser Tyr Arg Xaa Xaa Leu Xaa Xaa
1               5                   10                  15
Leu Ser Ala Arg Xaa Leu Leu Xaa Xaa Ile Xaa Xaa Arg
            20                  25

(2) INFORMATION FOR SEQ ID NO:16:

(i) SEQUENCE CHARACTERISTICS:
    (A) LENGTH: 32 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:16:

Xaa Ala Asp Ala Ile Phe Thr Xaa Ser Tyr Arg Lys Val Leu Xaa Xaa
1               5                   10                  15
Leu Ser Ala Arg Xaa Leu Leu Xaa Xaa Ile Xaa Xaa Arg Gln Gln Gly
            20                  25                  30